United States Patent
Bouville et al.

(10) Patent No.: US 11,845,720 B2
(45) Date of Patent: Dec. 19, 2023

(54) HEPTANE FROM A PLANT SOURCE, FOR THE EXTRACTION OF NATURAL PRODUCTS

(71) Applicants: UNIVERSITÉ CÔTE D'AZUR, Nice (FR); Centre National de la Recherche Scientifique, Paris (FR)

(72) Inventors: Anne-Sophie Bouville, Grasse (FR); Cyrielle Dieffoldo, Nice (FR); Xavier Fernandez, Nice (FR); Stéphane Piquart, Orvault (FR)

(73) Assignees: UNIVERSITÉ CÔTE D'AZUR, Nice (FR); Centre National de la Recherche Scientifique, Paris (FR)

( * ) Notice: Subject to any disclaimer, the term of this patent is extended or adjusted under 35 U.S.C. 154(b) by 674 days.

(21) Appl. No.: 16/966,129

(22) PCT Filed: Jan. 29, 2019

(86) PCT No.: PCT/EP2019/052132
§ 371 (c)(1),
(2) Date: Jul. 30, 2020

(87) PCT Pub. No.: WO2019/149701
PCT Pub. Date: Aug. 8, 2019

(65) Prior Publication Data
US 2021/0024441 A1    Jan. 28, 2021

(30) Foreign Application Priority Data
Jan. 30, 2018    (FR) ...................................... 1850753

(51) Int. Cl.
| | |
|---|---|
| *A61K 36/00* | (2006.01) |
| *C07C 7/00* | (2006.01) |
| *A23L 27/10* | (2016.01) |
| *A61K 8/9789* | (2017.01) |
| *A61K 8/31* | (2006.01) |
| *A61Q 13/00* | (2006.01) |
| *B01D 3/14* | (2006.01) |
| *B01D 11/02* | (2006.01) |
| *C07C 7/04* | (2006.01) |
| *C07C 7/09* | (2006.01) |
| *C07C 7/10* | (2006.01) |
| *C07C 9/15* | (2006.01) |

(52) U.S. Cl.
CPC .............. *C07C 7/005* (2013.01); *A23L 27/11* (2016.08); *A61K 8/31* (2013.01); *A61K 8/9789* (2017.08); *A61Q 13/00* (2013.01); *B01D 3/14* (2013.01); *B01D 11/0288* (2013.01); *C07C 7/04* (2013.01); *C07C 7/09* (2013.01); *C07C 7/10* (2013.01); *C07C 9/15* (2013.01); *A23V 2002/00* (2013.01); *A61K 2800/805* (2013.01)

(58) Field of Classification Search
CPC ........................................................ C07C 7/04
See application file for complete search history.

(56) References Cited

FOREIGN PATENT DOCUMENTS

| | | |
|---|---|---|
| EP | 2295026 A1 | 3/2011 |
| WO | 2012/136908 A1 | 10/2012 |

OTHER PUBLICATIONS

Galloway et al., Commercialising a Perfume Plant, Commiphora wildii: Livelihood Implications for Indigenous Himba in North-West Namibia. international forestry review (2016), vol. 18, No. 4, pp. 429-443 (Year: 2016).*

Marongiu et al., Chemical composition of the essential oil and supercritical CO2 extract of *Commiphora myrrha* (Nees) Engl. and of *Acorus calamus* L .: Journal of Agricultural and Food Chemistry, (Oct. 5, 2005) vol. 53, No. 20, pp. 7939-7943 (Year: 2005).*

Mahr, A brief visit to the succulent commiphoras of Namibia. Aloe (1998), vol. 35, No. 3/4, pp. 72-75 (Year: 1998).*

International Search Report issued in Application No. PCT/EP2019/052132, dated Apr. 9, 2019 (7 pages).

Written Opinion issued in International Application No. PCT/EP2019/052132, dated Apr. 9, 2019 (9 pages).

Jemmali Z. et al.; "Development of a gas chromatography-mass spectrometry method to monitor in a single run, mono- to triterpenoid compounds distribution in resinous plant materials"; Journal of Chromatography A; 1443; 2016; pp. 241-253 (13 pages).

* cited by examiner

*Primary Examiner* — Qiuwen Mi
(74) *Attorney, Agent, or Firm* — Osha Bergman Watanabe & Burton LLP

(57) ABSTRACT

A heptane composition obtained from a plant source is described, wherein the plant source comprises *Commiphora wildii* and wherein the heptane composition is obtained by a process of extraction comprising hydrodistilling or steam distilling a resin of *Commiphora wildii* to obtain an essential oil. A method of using the heptane composition as a solvent for extracting one or more natural products is also described.

7 Claims, No Drawings

US 11,845,720 B2

HEPTANE FROM A PLANT SOURCE, FOR THE EXTRACTION OF NATURAL PRODUCTS

TECHNICAL FIELD

The present description relates to heptane obtained from a plant source, for example by a process of extraction including distilling a resin from a plant source. The present description also relates to methods of using the heptane in perfumery, cosmetics and food flavoring.

BACKGROUND

In the fields of perfumery, cosmetics and food flavorings, currently two main families of natural extracts may be distinguished: the natural extracts obtained by hydrodistillation, steam distillation or expression, called essential oils, and the natural extracts obtained by extraction using at least one volatile solvent, called for example concretes, absolutes, oleoresins or resinoids.

The concrete or concrete essential oil is the crude product obtained by extraction of fresh plants with an organic solvent (i.e. hexane, heptane, petroleum ether, ethyl acetate, ethanol). For a dry plant material such as seeds or gum resins, the term resinoid is used. After evaporation of the organic solvent, a paste is obtained, more or less solid, containing volatile and nonvolatile constituents, some of which are insoluble in alcohol at high concentration. The absolute or absolute essential oil is an extract prepared from the concrete by hot dissolution in ethanol, in a step commonly called washing. The insoluble compounds, also known as waxes, are precipitated in a cold solidification step, also called chilling, then removed by filtration, and the solvent is then evaporated to obtain the absolute, which is generally used diluted in perfuming compositions.

Volatile solvent extraction is a method that is widely used for the extraction of natural products. The use of a solvent or of a mixture of solvents of suitable polarity makes it possible to extract odorous compounds by solid-liquid extraction. As the odorous compounds extracted are of low polarity, extraction solvents of low polarity are often used, such as hydrocarbons, and for example hexane, petroleum ether, or else heptane. Now, these solvents, currently derived mainly from fossil sources and therefore not renewable, are at the center of many environmental questions. In order to maintain environmental responsibility and sustainable development inspired by the twelve principles of green chemistry, new methods called "eco-extraction" are developing rapidly.

Moreover, changes in terms of composition of a solvent derived from a plant source compared with the corresponding solvent of fossil origin, even minor, may have a sensory effect, for example in perfumery, cosmetics and food flavoring. Any solvent derived from a renewable plant source may therefore constitute an alternative to the problems of solvents derived from nonrenewable resources, and at the same time, open up the horizon of the olfactory notes applicable in perfumery, cosmetics, and in the field of flavorings.

As a result, there is a need for solvents derived from plant sources intended to replace the solvents derived from nonrenewable resources.

*Commiphora* is a botanical genus of the family Burseraceae. This genus is made up of about 185 species of trees or shrubs, often thorny, originating from the shores of the Red Sea, from India, Madagascar and Senegal. The species *Commiphora myrrha* is the best known and the most used in the field of perfumery. Nowadays the species *Commiphora myrrha* is mainly used in the form of essential oil and resinoid. The essential oil of this species is obtained by hydrodistillation, and may have an odor that is both amber-scented, vanilla-scented, aromatic and woody, which is also reminiscent of the odor of mushrooms and licorice. The essential oil may have a dual role: to improve the durability and the fixation of a perfume, while supplying roundness and olfactory warmth.

The botanical genus *Commiphora* also includes the species *Commiphora wildii*, also called Omumbiri, a plant native to Namibia, where the Himba women collect the resin that exudes naturally from its bark, and have been using it for centuries for its fragrant properties, as body and hair perfume.

Certain components of a resin from *Commiphora wildii* were characterized in a very recent comparative study by Jemmali et al. "*Development of a gas chromatography-mass spectrometry method to monitor in a single run, mono-to triterpenoid compounds distribution in resinous plant materials*", J. Chromatogr. A, 2016, 1443, 241-253. Among others, alpha-pinene (2.34%), beta-pinene (0.40%), beta-phellandrene (0.53%), p-cymene (0.71%), gamma-terpinene (0.24%), verbenone (1.67%), verbenol (3.23%, via its verbenol-TMS derivative), and moronic acid (40.37%, via its moronic acid-TMS derivative), were identified. However, this study was simply aimed at the development of a general chromatographic method for measuring terpene compounds comprised in plant resins, including the resin from *Commiphora wildii*.

SUMMARY

One of the aims of the present disclosure is to supply solvents derived from plant sources, for example usable as volatile solvents with a view to obtaining a product, such as a concrete and then an absolute, having olfactory characteristics suitable for the field of perfumery, cosmetics and/or food flavorings.

According to a first aspect, the aforementioned aims as well as other advantages may be obtained by heptane obtained by a plant source comprising *Commiphora wildii*.

The inventors surprisingly found that the raw material is suitable, for example, for supplying a heptane that is already marketable and is ready to be used in perfumery, cosmetics and/or food flavoring, for example as a volatile solvent capable of extracting products which, depending on the plant source to be extracted that is selected, are suitable for use in these fields.

According to one or more embodiments, the plant source may consist of *Commiphora wildii*.

According to one or more embodiments, heptane may be obtained by a process of extraction comprising hydrodistilling or steam distilling a resin comprising the resin of *Commiphora wildii* to obtain an essential oil. Optionally, the process may further comprise physically purifying the essential oil.

The heptane may be also suitable, among others, for use as a volatile solvent capable of extracting products which, depending on the plant source to be extracted that is selected—which may be one of the species mentioned above—, are suitable for use in perfumery, cosmetics and/or food flavoring.

When heptane is obtained exclusively from a resin of the species *Commiphora wildii*, the yield of heptane obtained in the process may be substantially higher than the yields obtained from any other plant species.

According to one or more embodiments, hydrodistilling or steam distilling may be carried out in apparatus of the still type. Hydrodistilling may for example comprise adding water to the resin of *Commiphora wildii*, which may be in powder form, coarsely ground, or cut into pieces, in the fresh or withered state, in a still. The resin may be put in a flask or reactor of the apparatus and immersed in a water bath. The suspension thus obtained may be heated to boiling point so as to produce vapor. After stopping the heating, the vapors of water and of essential oil may be condensed in a condenser to separate the volatile essential oil from the organic upper layer of the distillate, so as to recover the essential oil.

According to one or more embodiments, the process of extracting heptane may further comprise physically purifying the essential oil. According to one or more embodiments, physically purifying may comprise purifying by fractional distillation or molecular distillation.

According to one or more embodiments, the heptane as obtained according to the first aspect may comprise substantially the linear isomer, i.e. n-heptane. For example, at least 99.0% of the heptane may be in the form of n-heptane. According to one or more embodiments, at least 99.5% of the heptane, for example between 99.5 and 99.9% of the heptane, for example between 99.6 and 99.9% of the heptane, may be in the form of n-heptane.

When the heptane contains at least 99.0% of n-heptane, the remaining 1.0% may comprise for example one or more components obtained from the same plant source as the n-heptane, such as any branched isomers of heptane.

According to one or more embodiments, the heptane may be obtained from the resin of *Commiphora wildii* of cultivated type or wild type. For example, the resin may be collected from a plant of the cultivated type.

According to one or more embodiments, the yield of essential oil of the species *Commiphora wildii* obtained in the process may be about 5.5% based on the fresh weight of resin.

In any of these embodiments, the process may further comprise collecting resin from plants of the cultivated type or wild type.

According to one or more embodiments, the process may further comprise collecting resin from the whole plant.

According to one or more embodiments, the present disclosure provides a composition comprising the heptane according to one or more embodiments presented above, as well as alpha-pinene and optionally beta-pinene. Such a composition may prove suitable, for example, for use as a volatile solvent capable of extracting products which, depending on the plant source to be extracted that is selected, are suitable for use in perfumery, cosmetics and/or food flavoring.

According to one or more embodiments, the composition may be derived from the species *Commiphora wildii*. The odorous characteristics of a composition derived from the species *Commiphora wildii* proved to be interesting for example, but not exclusively, for perfumery, due to lemon, woody, camphoraceous and menthol notes.

According to one or more embodiments, the composition may comprise at least 99.5% of heptane, and from 0.1% to 0.5% of alpha-pinene. According to one or more embodiments, the composition may comprise at least 99.5% of heptane, from 0.2% to 0.5% of alpha-pinene and from 0.0% to 0.3% of beta-pinene.

According to another aspect, the present disclosure relates to a method of using the heptane as defined by one or more of the embodiments presented above as a solvent for extracting natural products.

Surprisingly, the heptane has proved to be suitable, for example, for the extraction of natural products. For example, the natural product may comprise rose of the type *Rosa centifolia*, lily (*Lilium* spp), jasmine (*Jasminum grandiflorum* L.), violet (*Viola Odorata* L.), or tuberose (*Polianthes tuberosa* L.). However, the heptane is suitable for extracting any other plant useful in perfumery, cosmetics and food flavoring.

According to another aspect, the present disclosure relates to the a method of using the heptane as defined by one or more of the embodiments presented above for imparting a flavor and/or a fragrance to a product or modifying a flavor and/or a fragrance of a product.

The embodiments described above are not exhaustive. For example, it is to be understood that additional embodiments may be envisaged based on various combinations of the embodiments explicitly described. Unless specified otherwise in the present description, it will be apparent to a person skilled in the art that all the embodiments described above may be combined with one another. For example, unless specified otherwise, all the features of the embodiments described above, whether they relate to heptane or to methods of using the latter, may be combined with or replaced with other features of other embodiments.

Embodiments according to the aspects referred to above as well as additional advantages will become clearer on reading the following detailed description and the accompanying claims.

DETAILED DESCRIPTION

In the following detailed description of the embodiments of the present disclosure, many specific details are disclosed in order to provide a deeper understanding of the present description. However, it will be apparent to a person skilled in the art that the present description can be implemented without these specific details. In other cases, well-known features have not been described in detail, to avoid needlessly complicating the description.

Hereinafter, the term "comprise" is a synonym of (means the same thing as) "include", "contain", and is inclusive or open and does not exclude other elements that have not been described or represented. Furthermore, in the present description, the term "substantially" is a synonym of (means the same thing as) a lower and/or upper margin of 0.05% of the respective value. The following description gives two examples of process of extraction of heptane as defined by one or more of the embodiments presented above, as well as examples of a method of using of the heptane, such as for the extraction of natural products.

Example 1 of the Process of Extraction of Heptane

The process of manufacture according to Example 1 comprises hydrodistilling the resin of *Commiphora wildii* to obtain an essential oil, and distilling by fractional distillation of this essential oil.

The resin of *Commiphora wildii* is a natural exudate from the tree. As the bark of this tree is very thin and the resin-secreting channels are located just underneath, it is possible to recover this resin by incision on the lower part of the trunk. When the resin flows, it is of a milky white color, and it turns red on drying. The exudate used in the example of process of manufacture detailed below was collected after some weeks, so that the resin is dry.

The resin extracted from *Commiphora wildii* is hard and brittle, but becomes ductile and malleable when heated. The extraction technique used makes it possible to obtain a volatile extract from this resin.

According to one embodiment, hydrodistilling comprises: adding water to the resin of *Commiphora wildii* in the form of powder or small pieces/particles in a round-bottomed vessel fixed to apparatus of the Clevenger type, heating the suspension thus obtained to boiling point and condensing the vapors to recover the essential oil/water mixture. To separate the essential oil from the water, it is sufficient to decant the mixture. The apparatus of the "Clevenger" type allows reinjecting the aromatic water, namely the aqueous phase of the distillate, in the flask to avoid water depletion of the initial mixture. This technique is called hydrodistillation with cohobation. The same type of process may be carried out with a conventional still.

In the context of Example 1, the manipulation is carried out with a 20 L flask containing 2.00 kg of resin of *Commiphora wildii* immersed in five times its volume of water, or 10 L.

A kinetic study was conducted in these conditions, in order to determine the hydrodistillation time for controlling the yield of essential oil and the proportion of heptane. Table 1 presents the yields of essential oil obtained as a function of the hydrodistillation time. Similar results are obtained using a still.

TABLE 1

| Hydrodistillation time (h) | Yield of essential oil (%) |
|---|---|
| 4 | 5.68 |
| 6 | 6.99 |
| 12 | 7.77 |
| 18 | 8.22 |

The composition (in relative percentages obtained by integration of the chromatographic profile) of the essential oil obtained after 4 h of hydrodistillation was analyzed by GC/MS. The essential oil comprises: 43.4% of alpha-pinene, 29.5% of heptane, 11.0% of beta-pinene, 3.7% of alpha-thujene, and 2.3% of ortho-cymene. This new essential oil isolated by the inventors has, among others, a high heptane content.

The process of manufacture in Example 1 further comprises extractive distillation of the essential oil obtained after 4 h of hydrodistillation. Starting from this essential oil, it is possible to separate a fraction at 37.8 wt %, containing predominantly heptane, at least 99.3% pure. It contains not only heptane, but also alpha-pinene and beta-pinene in minor amounts, 0.3% and 0.1% respectively.

Example 2 of the Process of Extraction of Heptane

The process of manufacture according to Example 2 comprises hydrodistilling the resin of *Commiphora wildii* to obtain an essential oil, and fractional distilling this essential oil.

The essential oil obtained after 24 h of hydrodistillation comprises alpha-pinene, heptane, beta-pinene, para-cymene, and terpinen-4-ol.

The process of manufacture from Example 2 further comprises distilling by extractive distillation of the essential oil obtained after 24 h of hydrodistillation. Starting from this essential oil, it is possible to separate a fraction containing predominantly heptane, at least 90.0% pure. It contains not only heptane, but also alpha-pinene and beta-pinene.

Examples of Methods of Using the Heptane for the Extraction of Natural Products

The heptane produced as indicated above in Examples 1 and 2 was used as a solvent for extracting natural products, such as for example flowers of jasmine, lily, rose, violet, *mimosa*, and tuberose with a view to obtaining a concrete and then an absolute, marketable in the field of perfumery, cosmetics or food flavorings.

These extractions were carried out in the same conditions from one plant to another. The extracts obtained were compared with the extracts obtained from fossil heptane, derived from a petrochemical source.

The concretes obtained with the heptane derived from the species *Commiphora wildii* as solvent make it possible to conclude that the olfactory result is different from that obtained with fossil heptane. Without wishing to be bound by any theory, this may be explained by the quality of the heptane extracted and optionally by the presence of other odorous compounds in small amounts in the heptane extracted according to one or more embodiments of the present description.

A comparison of the sensory results obtained for volatile solvent extraction of three natural products, with fossil heptane versus the heptane derived from *Commiphora wildii* produced as indicated in Example 1, is presented in Table 2. The table shows, depending on the type of heptane used (heptane produced according to an embodiment of the present description or fossil heptane) and for each natural product extracted, the yield of concrete and the olfactory description of the absolute obtained from the concrete.

TABLE 2

| | Heptane produced according to Example 1 | | Fossil heptane | |
|---|---|---|---|---|
| | Yield of concrete | Olfactory description of the absolute | Yield of concrete | Olfactory description of the absolute |
| Rose (*Rosa centifolia* L.) | 0.47% | Fruity facets (banana), floral, rose, honey. | 0.22% | Green odor, floral, sticky and tenacious. |
| Lily (*Lilium* spp) | 0.41% | Floral odor, stifling, honey, less fatty. | 0.36% | Strong odor of lily, fatty, green, watery and iodized. |
| Jasmine (*Jasminum grandiflorum* L.) | 2.60% | Fatty odor, flowery, jasmine and menthol. | 0.67% | Flowery odor, sticky, fatty, animal and heady. |

Another comparison of the sensory results obtained for volatile solvent extraction of four natural products, with fossil heptane versus heptane derived from *Commiphora wildii* produced as indicated in Example 2, is presented in Table 3. The table shows, depending on the type of heptane used (heptane produced according to an embodiment of the present description or fossil heptane) and for each natural product extracted, the yield of concrete and the olfactory description of the absolute obtained from the concrete.

TABLE 3

|  | Heptane produced according to Example 2 | | Fossil heptane | |
|---|---|---|---|---|
|  | Yield of concrete | Olfactory description of the absolute | Yield of concrete | Olfactory description of the absolute |
| Violet | 1.93% | Aromatic infusion of herbs, green tea, verbena. Light camphoraceous note, earthy. | 0.18% | Absolute of violet leaf more hay than usual. |
| Mimosa | 3.32% | Green, classic cucumber note in the absolutes from mimosa. | 1.16% | Less green, singular balsamic notes, hay, dried herbs. Does not denature the absolute note of mimosa. |
| Tuberose | 1.80% | Very different from a classic tuberose absolute, there is a dominant fruity note but we also find a flowery and amber-scented note. Tuberose is less distinct but the odor is reminiscent of aromatic water from Roman chamomile. | 0.23% | Classic tuberose absolute. Very spicy with a floral fatty side note. Note of papyrus, jasmine, heady flowers. |
| Rose de Mai (May Rose) | 2.61% | The rose is recognizable initially and then there is an aromatic, camphor, incense aspect. Presence of a blackcurrant note. | 0.29% | Odor very close to the fresh flower with a fatty side note. This is a beautiful fruity, aldehyde flower with a light green note supplying freshness. |

Chemical analyses (GC/MS) of the concretes extracted with the heptane according to the two embodiments of the description described in Examples 1 and 2 and of the concretes extracted with the fossil heptane show similar chemical compositions. The analyses reveal a larger amount of hydrocarbons present in the concretes extracted with the fossil solvents. In contrast, the concretes extracted with the heptane according to an embodiment of the description have a larger number of volatile organic compounds with a characteristic odor, thus contributing to the supply of new olfactory facets for the concretes of the extracted natural products.

Furthermore, the heptane produced as indicated in Example 2, and used for producing the concretes and absolutes of first quality, for which the yields and olfactory results, respectively, are presented in Table 3, was recycled for a second extraction, as well as the fossil heptane, in order to produce, for the same four natural products given in Table 3, a concrete and an absolute of second quality. For each natural product extracted and depending on the heptane used, the yield of concrete and the olfactory description of the absolute of second quality obtained from the concrete are presented in Table 4.

TABLE 4

|  | Heptane produced according to Example 2, recycled | | Fossil heptane, recycled | |
|---|---|---|---|---|
|  | Yield of concrete | Olfactory description of the absolute | Yield of concrete | Olfactory description of the absolute |
| Violet | 0.17% | Aromatic, fruity, the violet leaf is indistinct. | 0.13% | Green, mown lawn under rain. |
| Mimosa | 3.99% | Very different from the absolute of first quality. Aldehydes, fatty. | 1.18% | Seems to be a diluted version of the absolute of first quality. |

TABLE 4-continued

| | Heptane produced according to Example 2, recycled | | Fossil heptane, recycled | |
|---|---|---|---|---|
| | Yield of concrete | Olfactory description of the absolute | Yield of concrete | Olfactory description of the absolute |
| Tuberose | 0.47% | Floral, honey, leathery, animal, like a trip to the souk with notes of mutton fat. Interesting new material as base note or middle note. | 0.37% | Floral, a bit sweet, of the grenadine type. |
| Rose de Mai | 0.48% | Firstly a fresh side note, camphoraceous, blackcurrant, and then a light rose note. | 0.49% | Rosy but loss of the fruity side note. |

Analysis Conditions:

In the parts described above, the essential oils obtained from *Commiphora wildii* or the concretes from natural products extracted with heptane are identified by gas chromatography coupled to mass spectrometry (GC/MS). The analysis conditions are as follows: nonpolar column (Ref: Supelco SLB—5MS—380° C. max)—30 m×0.25 mm×0.30 mm—df=0.25 mm—Temperature gradient: 2° C./min from 40° C. to 220° C. then 20° C./min up to 270° C.—Analysis time: 112.5 min—Gas: He—Split 1:100—Flow rate: 1 mL/min—Quantity injected: 0.1 µL.

Thus, the methods of using the heptane according to one or more embodiments of the present description, including the method of using the heptane as a solvent for extracting natural products, constitute an innovative alternative that may be useful for several applications, for example in the fields of perfumery, cosmetics or food flavorings.

The heptane according to one or more embodiments of the present description makes it possible to offer a larger range of raw materials to the perfumer, thus broadening the horizons of modern perfumery, as well as cosmetics and flavorings.

The invention claimed is:

1. A heptane composition obtained from a plant source, wherein the plant source comprises *Commiphora wildii*, wherein the heptane composition is prepared by a process of extraction comprising hydrodistilling or steam distilling a resin of *Commiphora wildii* to obtain an essential oil, wherein the process further comprises physically purifying the heptane composition by fractional distillation or by molecular distillation; and wherein the purified heptane composition comprises at least 99.3% heptane, 0.3% alpha-pinene, and 0.1% beta-pinene.

2. The heptane composition as claimed in claim 1, wherein a content of linear isomer n-heptane is above 99.0%.

3. The heptane composition as claimed in claim 1, wherein the essential oil is obtained in an amount of about 5.5% based on a fresh weight of resin.

4. The heptane composition as claimed in claim 1, wherein the process further comprises collecting resin from plants of a cultivated type or wild type.

5. The heptane composition as claimed in claim 1, wherein the process further comprises collecting resin from a whole plant.

6. A method of using the heptane composition as claimed in claim 1, the method comprising extracting one or more natural products from a second plant source with the heptane composition of claim 1 as a solvent.

7. The method as claimed in claim 6, wherein the natural product comprises rose, jasmine, lily, violet, *mimosa*, tuberose or any other plant useful in perfumery, cosmetics and food flavoring.

* * * * *